United States Patent
Shazly et al.

(10) Patent No.: US 10,353,460 B2
(45) Date of Patent: Jul. 16, 2019

(54) EYE AND HEAD TRACKING DEVICE

(71) Applicants: Tarek A Shazly, Pittsburgh, PA (US); Salwa A Abdelwahed, Pittsburgh, PA (US)

(72) Inventors: Tarek A Shazly, Pittsburgh, PA (US); Salwa A Abdelwahed, Pittsburgh, PA (US)

(*) Notice: Subject to any disclaimer, the term of this patent is extended or adjusted under 35 U.S.C. 154(b) by 0 days.

(21) Appl. No.: 15/114,904

(22) PCT Filed: Jan. 28, 2015

(86) PCT No.: PCT/US2015/013220
§ 371 (c)(1),
(2) Date: Jul. 28, 2016

(87) PCT Pub. No.: WO2015/116640
PCT Pub. Date: Aug. 6, 2015

(65) Prior Publication Data
US 2016/0342206 A1    Nov. 24, 2016

Related U.S. Application Data

(60) Provisional application No. 61/932,849, filed on Jan. 29, 2014.

(51) Int. Cl.
*G06F 3/01* (2006.01)
*A61B 3/113* (2006.01)
(Continued)

(52) U.S. Cl.
CPC .............. *G06F 3/013* (2013.01); *A61B 3/113* (2013.01); *A61B 5/1114* (2013.01); *G02C 11/10* (2013.01);
(Continued)

(58) Field of Classification Search
CPC ........ G06F 3/013; G06F 3/017; G06F 3/0304; G06F 3/012; G06K 9/00335;
(Continued)

(56) References Cited

U.S. PATENT DOCUMENTS 5,682,144 A * 10/1997 Mannik .................. G08B 21/06
257/221
5,883,616 A * 3/1999 Koizumi ................. G06F 3/012
200/1 R

(Continued)

*Primary Examiner* — Sanjiv D. Patel
(74) *Attorney, Agent, or Firm* — Morse, Barnes-Brown & Pendleton, P.C.; Sean D. Detweiler, Esq.

(57) ABSTRACT

An apparatus and method of use for tracking eye and head movement comprising (1) at least one optoelectronic array sensor or optical flow sensor formed of a plurality of optoelectronic sensor cells; (2) a body configured to support the optoelectronic array sensor with focusing means along with a source of light with collimating means in front of and in proximity to an eye of a user; (3) an optical focusing means to focus an image of the ocular surface of the user on the optoelectronic array sensor; (4) a focusing lens with a source of light; (5) a means to detect blinking; (6) a driver configured to receive signals from the sensor array to generate coordinate signals corresponding to changes in the position of the ocular surface relative to the sensor array; and (7) a means to detect user's additional input and gestures.

20 Claims, 5 Drawing Sheets

(51) Int. Cl.
  *A61B 5/11* (2006.01)
  *G02C 11/00* (2006.01)
  *G06F 3/03* (2006.01)
  *G06K 9/00* (2006.01)
  *G06T 11/60* (2006.01)
  *G02B 27/01* (2006.01)
  *A61B 5/00* (2006.01)

(52) U.S. Cl.
  CPC ............. *G06F 3/012* (2013.01); *G06F 3/017* (2013.01); *G06F 3/0304* (2013.01); *G06K 9/00335* (2013.01); *G06K 9/00604* (2013.01); *G06T 11/60* (2013.01); *A61B 5/0077* (2013.01); *A61B 2562/0219* (2013.01); *G02B 2027/0178* (2013.01); *G06T 2207/30204* (2013.01)

(58) Field of Classification Search
  CPC ............... G06K 9/00604; G06T 11/60; G06T 2207/30204; G02C 11/10; A61B 5/1114; A61B 3/113; A61B 5/0077; A61B 2562/0219; G02B 2027/0178; G02B 27/017; H04N 13/214; H04N 13/254
  See application file for complete search history.

(56) References Cited

U.S. PATENT DOCUMENTS

| | | | | |
|---|---|---|---|---|
| 6,373,961 B1 * | 4/2002 | Richardson | ............. | G06F 3/013 345/8 |
| RE39,539 E * | 4/2007 | Torch | ................... | A61B 3/0066 340/573.1 |
| RE41,376 E * | 6/2010 | Torch | ................... | A61B 3/0066 340/573.1 |
| 8,912,979 B1 * | 12/2014 | Gomez | ................... | G09G 3/001 345/7 |
| 2001/0009478 A1 * | 7/2001 | Yamazaki | ............ | G02B 27/017 359/630 |
| 2005/0213792 A1 * | 9/2005 | Hammoud | .......... | G06K 9/00604 382/103 |
| 2008/0030587 A1 * | 2/2008 | Helbing | ..................... | G06T 5/50 348/208.4 |
| 2010/0295769 A1 * | 11/2010 | Lundstrom | ............. | G06F 3/011 345/156 |
| 2011/0310238 A1 * | 12/2011 | Koh | ........................ | H04N 7/18 348/78 |
| 2013/0106674 A1 * | 5/2013 | Wheeler | .............. | G02B 27/017 345/8 |
| 2013/0207887 A1 * | 8/2013 | Raffle | ..................... | G02B 27/00 345/156 |
| 2013/0342525 A1 * | 12/2013 | Benko | ................ | H04N 13/0495 345/419 |
| 2014/0002486 A1 * | 1/2014 | Ratcliff | .................. | G09G 3/003 345/629 |
| 2014/0118680 A1 * | 5/2014 | Chang | .................... | G02C 11/10 351/44 |
| 2014/0164928 A1 * | 6/2014 | Kim | ........................ | G06F 3/017 715/728 |
| 2014/0267400 A1 * | 9/2014 | Mabbutt | ................ | G06T 19/006 345/633 |

* cited by examiner

A. Image at 0 msec

B. A. Image at 0.67 msec

EYE AND HEAD TRACKING DEVICE

RELATED APPLICATIONS

This application is a National Stage Application under 35 USC 371 of Application No. PCT/US2015/013220 filed Jan. 28, 2015, which claims priority to U.S. Provisional Application No. 61/932,849 filed Jan. 29, 2014. The entire contents of the above application are hereby incorporated by reference as though fully set forth herein.

BACKGROUND

The present application generally relates to eye and head tracking. In particular, though not exclusively, the present application relates to non-contact eye and head tracking.

Eye movements of human beings are mediated by different voluntary and involuntary mechanisms. Different parts of the nervous system are responsible for starting, maintaining and terminating eye movements. Fixation is the maintaining of the visual gaze on a single location. Other parts of the nervous system are responsible for maintaining eye fixation on an object regardless of the head position in space.

The vestibulo-ocular reflex (VOR) or the oculo-cephalic reflex is a reflex eye movement that stabilizes images on the retina during head movement by producing an eye movement in the direction opposite to the direction of head movement, thus preserving the image on the center of the visual field. This reflex compensates for horizontal, vertical and rotational head movements. For example, when the head moves to the right, the eyes proportionately move to the left while if the individual's head tilts to towards the shoulder, both eyes rotate along their antero-posterior axis in a movement called torsion to compensate for the head tilt.

Tracking of the eye movements has various applications such as detecting of abnormal eye movements due to neurological disorder. Tracking of the eye movements can also be used to move a cursor on a computer screen so that the eyes of the user can control such a device. Eye trackers measure rotations of the eye in one of several ways, but principally they fall into three categories: (i) measurement of the movement of an object (normally, a special contact lens) attached to the eye; (ii) optical tracking without direct contact to the eye; and (iii) measurement of electric potentials using electrodes placed around the eyes.

The first category generally uses an attachment to the eye, such as a special contact lens with an embedded mirror or magnetic field sensor, and the movement of the attachment is measured. Measurements with tight fitting contact lenses have provided extremely sensitive recordings of eye movement. It allows the measurement of horizontal, vertical and torsional eye movements.

The second broad category uses non-contact, optical method for measuring eye motion. Light, typically infrared, is reflected from the eye and sensed by a video camera. The information is then analyzed to extract eye rotation from changes in reflections. Video-based eye trackers typically use the corneal reflection (the first Purkinje image) and the center of the pupil as features to track over time. Optical methods, particularly those based on video recording, are widely used for gaze tracking and are favored for being non-invasive. Such trackers typically require relatively high resolution cameras capturing at a high frame rate with image processing and pattern recognizing device to track the reflected light or known ocular structures such as the iris or the pupil. They lack the accuracy of the contact method and cannot detect torsional eye movement along its antero-posterior access.

The third broad category involves the use of electrodes placed on the surface of the eye to measure electric potentials. A limitation of this method is the inaccuracy of measurements for small and large eye movements. Background electric noise from the brain and facial muscles that is equivalent to approximately 1 degree of eye movement appears on the signal. Therefore, eye movements that are less than 1 or 2 degrees are difficult to record using this method. Also, eye movements that are greater than approximately 30 degrees do not produce amplitudes that are strictly proportional to eye position As discussed above, while the use of current non-contact eye tracking devices are less invasive and presumably more comfortable to the patient during examination, their use generally results in a level of reduced efficacy and accuracy. While there are attempts to meet this need in the prior art, such set forth in PCT application WO2013110846 to Bergman et. al., these attempts fall short. For example, Bergman discloses the use of a capacitative sensor for non-contact eye tracking; however, capacitative sensors have limitations in that they are very sensitive to environmental conditions such as humidity and temperature. Since the ocular surface is continuously evaporating tears, the accuracy of the capacitative sensor is impaired. Further, capacitative sensors are very sensitive to the distance from the eye, so even minor changes in position of the frames used in Bergman can affect accuracy. Additionally, movement of the eyelid in front of the eye (blinking) can be misinterpreted by capacitative sensors as eye movement.

Optical flow or optic flow is the pattern of apparent motion of objects, surfaces, and edges in a visual scene caused by the relative motion between an observer (an eye or a camera) and the scene. The concept of optical flow was introduced by the American psychologist James J. Gibson in the 1940s to describe the visual stimulus provided to animals moving through the world. Recently the term optical flow has been co-opted by roboticists to incorporate related techniques from image processing and control of navigation, such as motion detection, object segmentation, time-to-contact information, focus of expansion calculations, luminance, motion compensated encoding, and stereo disparity measurement.

Optical flow was used by robotics researchers in many areas such as: object detection and tracking, image dominant plane extraction, robot navigation, movement detection and visual odometry. Optical flow information has been recognized as being useful for controlling micro air vehicles and robots.

An optical flow sensor is a vision sensor capable of measuring optical flow or visual motion and outputting a measurement based on optical flow. Various configurations of optical flow sensors exist. One configuration is an image sensor chip connected to a processor programmed to run an optical flow algorithm. Another configuration uses a vision chip, which is an integrated circuit having both the image sensor and the processor on the same die, allowing for a compact implementation. An example of this is a generic optical mouse sensor used in an optical mouse. In some cases the processing circuitry may be implemented using analog or mixed-signal circuits to enable fast optical flow computation using minimal current consumption.

One area of contemporary research is the use of neuromorphic engineering techniques to implement circuits that respond to optical flow, and thus may be appropriate for use in an optical flow sensor. Such circuits may draw inspiration from biological neural circuitry that similarly responds to optical flow.

Optical flow sensors are used extensively in computer optical mice, as the main sensing component for measuring the motion of the mouse across a surface.

Optical flow sensors are also being used in robotics applications, primarily where there is a need to measure visual motion or relative motion between the robot and other objects in the vicinity of the robot. The use of optical flow sensors in unmanned aerial vehicles (UAVs), for stability and obstacle avoidance, is also an area of current research.

Therefore, there is a need in the art for non-contact eye tracking device providing a more simplified operation and more precise motion tracking. Additionally, there is a need for a non-contact device that can detect torsional eye movement along the antero-posterior access of the eye without contacting the eye.

BRIEF SUMMARY OF THE INVENTION

The present invention serves to meet these needs, in addition to having other beneficial properties such as compactness, accuracy and non-blocking of the eye view. According to one embodiment of the present invention, a compact apparatus comprises (1) at least one optoelectronic array sensor or optical flow sensor; (2) a body configured to support the optoelectronic array sensor with focusing means along with a source of light with collimating means in front of an eye of a user; (3) an optical focusing means to focus an image of the ocular surface of the user on the optoelectronic array sensor; (4) a focusing lens with a source of light; (5) means to detect blinking; and (6) a driver configured to receive signals from the sensor and to determine eye movements based on the received signals. The focusing means may include a plus powered focusing lens, mirror or pinhole. The apparatus may further comprise a means to detect user's additional input and gestures. The terms "optoelectronic array sensor" and "optical flow sensor" may be used interchangeably herein.

The apparatus may further comprise a driver configured to receive signals from the sensor and to determine eye movements based on the received signals and a communication module to communicate with an external device typically a computer along with its software. In the preferred embodiment of the present invention, the optoelectronic array sensor is a complementary metal-oxide semiconductor (CMOS).

In the preferred embodiment of the present invention, the apparatus may be wearable by the user. The apparatus may be wearable like eyeglasses. The apparatus may be wearable directly on the face of the user. The apparatus may be wearable over the glasses of the user. The body may be supported by the nose of the user and/or by one or two ears of the user. The sensor may be integrated with a lens of eyeglasses. Alternatively, the sensor may be attached to a lens of eyeglasses or to a frame of eyeglasses so that the sensor resides between the eye of the user and a lens of the eyeglasses, when the eyeglasses are worn by the user. It can also be attached to the frame of oversized eyeglasses to be wearable over the user eyeglasses so that the sensor lies between the oversized eyeglass frame and the lens of the user glasses.

The sensor may be attached to a display of video glasses. The sensor may be attached adjacent to a display of video glasses. The sensor may be covered by a protective coating. The body may be configured to support the optoelectronic array sensor in front of the eye of a user at a proximate distance. The proximate distance may be such that the eyelash of the user does not reach to the sensor or the lens materials in front of the eye. The proximate distance may correspond to the focusing power of the focusing lens of the sensor. The body may be formed of eyeglass frames. The body comprises mechanical mounting means that may be configured to adjust the distance between the CMOS sensor and the eye of a user. Alternatively the focusing lens distance to the optoelectronic array sensor is adjustable to maintain a focused image of the ocular surface on the sensor.

According to further aspects of the present invention, the light source may comprise at least one coherent light source such as a laser emitting diode (LD). The laser emitting diode may emit a visible laser light. The laser emitting diode may emit an invisible laser light. The light source may comprise incoherent light source such as a light emitting diode (LED). The light emitting diode may emit a visible light. The light emitting diode may emit an invisible light. The light emitting diode may emit light of a single color. The light emitting diode may emit light of a combination of multiple wavelengths of light. The light source may have a combination more than one incoherent light emitting diodes. The light source may have a combination of more than one coherent laser emitting diodes. The light source may have a combination of coherent and incoherent light emitting diodes.

According to further aspects of the present invention, the driver may comprise the analog-to-digital converter. The driver comprises one or more digital signal processors (DSP) such as special purpose image-processing chips. The focusing lens of the sensor will form an image of the ocular surface illuminated with the source of light on the optoelectronic array sensor. The optical texture of the ocular surface formed by irregularities and optical imperfections such as conjunctival blood vessels, conjunctival glands and uneven thickness of the tear film over the surface with form a corresponding image on the optoelectronic array sensor with distinct shadows. The incoherent light of the light source projects light on the surface of the eye so that the different irregularities of the eye surface along with their shadows are more evident. Coherent light of the light source projected on the ocular surface is reflected back to the sensor forming different laser patterns because of the ocular surface irregularities. Images of the eye surface are captured by the optoelectronic array sensor in continuous succession at a high rate of 1500 frames per second or more. The frames are converted from analog to digital and transferred to the driver. The driver comprises an image-processing chip to compare the frames to each other. The image-processing chip mathematically process these images using cross correlation to calculate how much each successive image is offset from the previous one. The driver will generate digital data of how far the eye has moved and in which direction. The driver will generate the data as shift of the horizontal (X) and vertical (Y) co-ordinate from the last known location. Such data is provided to the communication module.

According to further aspects of the present invention, the distance may be adjusted so that the focusing lens focuses an image of the ocular surface on the optoelectronic array sensor to detect eye movement. The apparatus may comprise two of the sensors. The apparatus may be configured support one of the sensors in front of each of two eyes of the user.

According to further aspects of the present invention, the apparatus may comprise at least one sensor in front of each eye. The apparatus may be configured support a sensor in front the outer corner of the eye and the inner corner of the eye of the user.

The apparatus may further comprise a touch controller. The touch controller may be configured to detect touching of the user at one or more touch sensitive areas in the body and/or on the driver.

The apparatus may further comprise a sound activated switch. The sound activated switch may be configured to detect sounds produced by the user.

The apparatus may further comprise a voice recognition module. The voice recognition module may be configured to receive voice commands from the user.

The apparatus may further comprise a motion-activated switch facing the eyebrows and attached to the body of the device as a means to detect user's additional input and gestures. The motion-activated switch may comprise infrared light emitter and infrared sensitive photodiode receiver connected to a dedicated circuit to convert the change in the intensity of reflected infrared light to a digital signal. It may also comprise a sonic or ultrasonic wave emitter and receiver connected to a dedicated circuit to convert the change in the intensity of reflected sonic or ultrasonic waves to a digital signal. When the user moves his or her eye brows in a gesture such as in brow elevation or depression, the motion-activated switch converts the movement to a digital signal that is then transferred to the driver, then the communicating device and eventually to the external device.

The apparatus may further comprise an airflow-activated switch attached via mechanical means to the body of the device and facing the mouth of the user as a means to detect user's additional input and gestures. The airflow-activated switch may also be attached so that it faces the nostrils of the user. The airflow-activated switch may comprise a mobile mechanical element such as a mobile flap made of an electrically connective material in proximity to another electrically conductive fixed structure within a tubular housing. Both conductive structures are terminal attached to an electronic circuit to detect contact of the 2 terminals. The airflow-activated switch may also comprise mobile part in a tubular housing in proximity to obstacle-activated switch with paired light emitter and receiver circuit. Such circuit is activated when the mobile part if forced by the airflow to block the light path between the emitter and receiver. The airflow activated switch may also comprise a fan attached to a dynamo motor connected to dedicated circuit known to those skilled in the art to convert the electric current generated by rotation of the fan to digital signal. When the user the airflow will force the flap terminal to touch the fixed terminal and induce a closure of an electric circuit. Airflow can also activate a paired light emitter/receiver circuit or it may generate a digital signal by rotating a fan connected to a dynamo. Air blowing stimulates a digital signal that is then transferred to the driver, then the communicating device and eventually to the external device.

The apparatus may further comprise a mechanical switch as a means to detect user's additional input and gestures. The mechanical switch can be activated by different bodily parts of the user. The mechanical switch may be activated by pressure exerted by the user's one or more body parts. For example the mechanical switch can be incorporated in a foot pedal so that when the user presses on the foot pedal with his or her foot the switch is activated. The switch can be connected to the device via wired or wireless means. The activation of the switch generates a digital signal that is then transferred to the driver, then the communicating device and eventually to the external device.

The apparatus may further comprise. The front facing camera is mounted on the body of the device facing the external world at which the user is looking towards. The digital data generated by the camera is transmitted via wired or wireless means to the external device such as a computer. The computer software calibrates the direction of gaze of the user to the acquired images of the environment. After such calibration, the software would be able to superimpose the direction of gaze on the continuously captured images of the environment to determine what object or objects the user is looking at.

The apparatus may further comprise a back facing camera attached to the body of the device as a means to detect user's additional input and gestures. The back facing camera is mounted on the body of the device facing the face of the user. The digital data generated by the camera is transmitted via wired or wireless means to the external device such as a computer. The computer software may use eye-tracking algorithm of one or both eyes known from prior art to be used as additional means of eye tracking. For example when the user blinks the lid blocks the view of the optical array sensor, and the eye may move underneath the closed lid before the eyelid opens causing un-captured eye movement. The software can detect and compensate for the un-captured movement by comparing the position of the eye before and after each blink to recalibrate the device. The device may also combine the eye tracking data from the camera analyzed by the software and the tracking data obtained by the optoelectronic array sensor and use a mathematical combination of both data.

The apparatus may further comprise a gyroscopic sensor attached to the body of the device as a means to detect user's additional input and gestures. The gyroscopic sensor is mounted on the body of the device. As the body of the device in the frame moves in unity with the head of the user, the gyroscopic sensor senses the movement of the user's head in the horizontal, vertical and rotational directions. The digital data generated by the gyroscopic sensor is transmitted via wired or wireless means to the external device such as a computer. The computer software uses the head movement tracking data generated by the gyroscopic sensor in conjunction with the head tracking data generated by the optoelectronic array sensor. When the user fixates on an object and moves his or her head, the vestibulo-ocular reflex moves the eyes in opposite direction so that the optoelectronic array sensor sensed eye tracking data can be processed by the external device software can be used for head movement tracking. The data generated by the gyroscopic sensor as well as the optoelectronic array sensor can be further processed by the external device software in a mathematical way to use one or both sets of data to improve the accuracy of head movement tracking.

The apparatus may further comprise a feedback device attached to the body of the device as a means to detect user's additional input and gestures. The feedback device is a sound speaker, buzzer, vibrator and/or a light source.

According to further aspects of the present invention, the apparatus may further comprise a wired connection interface for connecting with an external device. The apparatus may be configured to provide the external device with eye tracking signals corresponding to other sensory data collected by the apparatus, such as touch information. The apparatus may be configured to provide the external device with eye tracking signals corresponding to other sensory data collected by the apparatus, such as a touch, sound, voice command or a blink. The wired connection interface may comply with a standard. The standard may be selected from a group comprising Inter-Integrated Circuit (I2C) protocol, Serial Peripheral Interface (SPI), Universal serial bus (USB) and IEEE-1394. The apparatus may be configured to receive operating power from the external device. The apparatus may receive power from a rechargeable battery. The apparatus may receive power from a non-rechargeable battery.

The blink detector may be comprised of a source of light such as infrared diode emitting the infrared light at a certain frequency of pulses per second and a photodiode sensitive to the light emitted by the source of lights. The two components are arranged in a way so that the light emitted by the diode is directed towards the eye surface just below the upper eyelid and the photodiode is also pointed towards the eye surface just below the upper eyelid. The axis of the two components cross in front of the eye surface. When the subject blinks the upper eyelid moves down and intercepts the infrared light and reflects it back to the photodiode to change its resistance to electric current. Such a change in resistance can be processed using a simple circuit known to those skilled in the art to switch ON when the blink happens. Once the eyelid opens the infrared rays are no longer reflected back to the photodiode so that the circuit is OFF. These signals are transmitted to the driver of the device and then to the communication module and eventually to the external device.

According to further aspects of the present invention, the blink detector may comprise a source of sonic or ultrasonic waves and a microphone to detect the reflected waves to detect a blink.

The present invention may further comprise a sound activated switch. The sound activated switch may comprise a microphone to detect sounds made by the user such as tongue click sounds or lip bursts. Such sounds activate the microphone and using an electronic amplifying circuit with adjustable gain control know to those skilled in the art may be used to convert the sound to a signal that is converted to a digital signal that transfers to the driver and then to the communicating module and eventually to the external device.

According to further aspects of the present invention, the voice recognition module may compromise a microphone to capture the user voice. The module may also comprise amplifying circuits as well as dedicated digital signal processor, microcontroller, volatile, non-volatile memory Analog-to-digital converter, digital-to-analog converter, digital filtering, Random-access memory, Read-only memory, output amplification, timers, and comparators. In addition, flash memory, Electrically Erasable Programmable Read-Only Memory (EEPROM), main clock and real time clock crystals, along with noise management components well known to those skilled in the art to receive voice commands from the user, compare them to pre-recorded voice commands and if matched, the command is transmitted as digital signal to the driver, then the communicating device and eventually to the external device.

The present invention may further comprise a wireless connection interface for connecting with an external device. The wireless connection interface may comply with a standard. The standard may be selected from a group consisting of: low power Bluetooth, IEEE 802.11 (wireless LAN), ultra-wide band (UWB) radio link such as 2.4 GHz, and Infrared Data Association (IrDA) link.

According to a second embodiment of the present invention, there is provided a computer program, comprising: code for receiving signals from a driver located in front of an eye of a user; and code for determining movement of the eye based on the received signal when the computer program is run on a processor.

According to a third embodiment of the present invention, there is provided a computer program, comprising: code for receiving signals from an optoelectronic array sensor located in front of an eye of a user; and code for determining movement of the eye based on the received signal when the computer program is run on a processor.

According to a fourth embodiment of the present invention, there is provided an apparatus comprising: means for optoelectronic array sensing; body means for supporting the means for optoelectronic array sensing in front of an eye of a user; and driver means for receiving signals from the optoelectronic array sensing means and for determining eye movements based on the received signals.

Any foregoing memory medium may comprise a digital data storage such as a data disc or diskette, optical storage, magnetic storage, holographic storage, opto-magnetic storage, phase-change memory, resistive random access memory, magnetic random access memory, solid-electrolyte memory, ferroelectric random access memory, organic memory or polymer memory. The memory medium may be formed into a device without other substantial functions than storing memory or it may be formed as part of a device with other functions, including but not limited to a memory of a computer, a chip set, and a sub assembly of an electronic device.

DETAILED DESCRIPTION

An example embodiment of the present invention and its potential advantages are understood by referring to FIGS. 1 through 5 of the drawings.

Figure 1A:
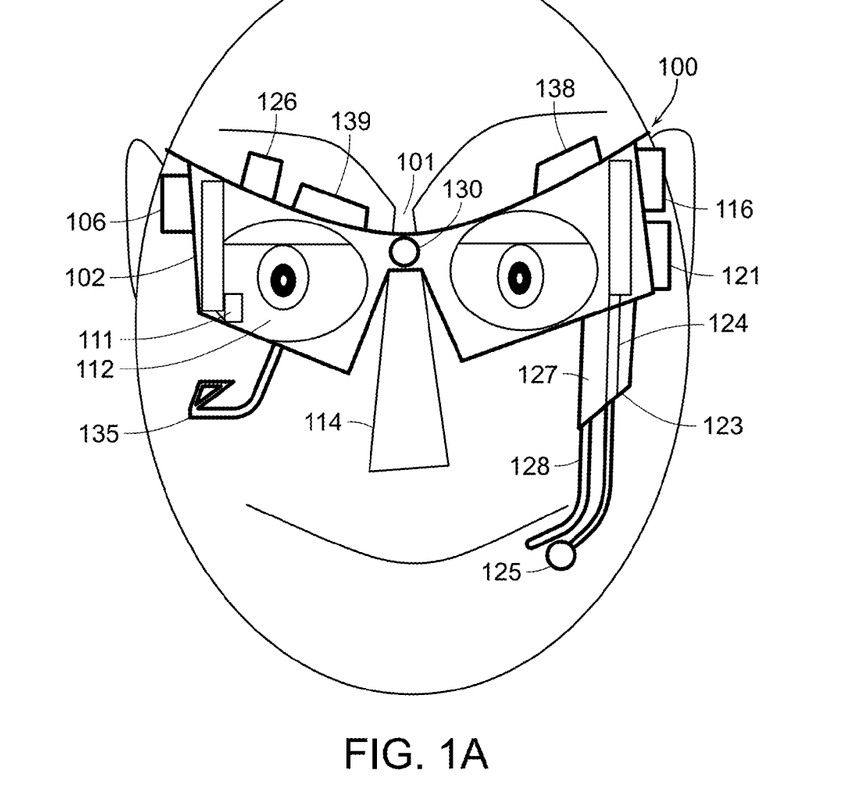
FIG. 1A shows a schematic drawing of a head-worn apparatus, when seen from front on a user.
Figure 1B:
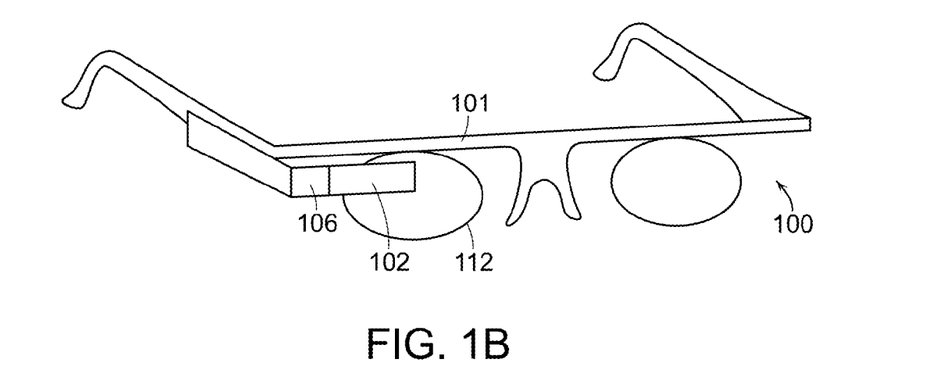
FIG. 1B is a front view of the present invention.

FIGS. 1A and 1B shows a schematic drawing of a head-worn apparatus 100, when seen from front. The apparatus 100 comprises an optoelectronic array sensor 102 supported by a body 101 or frame in front of an eye 112 of a user 110. The apparatus 100 further comprises a driver 106 configured to receive signals from the optoelectronic array sensor 102 and to determine eye movements based on the received signals. The driver 106 can detect relative motion of the eye 112 based on the offset of the pattern of imperfections of the surface of the eye 112 between successive frames obtained by the sensor 102.

The apparatus may be wearable by the user. The apparatus may be wearable like eyeglasses.

In an example embodiment and in FIG. 1, the body 101 is supported by the nose 114 of the user and/or by one or two ears 116 of the user.

In an example embodiment and in FIG. 1, the apparatus 100 comprises a blink detector 111 facing the surface of the eye 112 of a user 110. When the user 110 blinks, the eyelid obscures the surface of the eye 112 and stimulates the blink detector 111. The apparatus comprises a sound activated switch 123 that further comprises a microphone 125 facing the mouth of the user 110. When the user 110 produces a loud sound, the microphone 125 converts the sound waves to electric current that further gets amplified, filtered and converted to a digital signal by the sound activated switch 123. The digital signal is transmitted to the digital signal processor of the driver 106. The driver 106 transmits the signals to the communication module 300 that transmits the signals via wired or wireless means to the external device 400.

In an example embodiment and in FIG. 1, the apparatus 100 comprises a voice recognition module 124 that receives electric signals from the microphone 125 facing the mouth of the user 110. When the user 110 says a word, the microphone 125 converts the sound waves to electric current that further gets amplified, filtered and processed by a digital signal processor of a circuit that compares the microphone generated current to pre-recorded words and converted to a digital signal. The digital signal is transmitted to the digital signal processor of the driver 106. The driver 106 transmits the signals to the communication module 300 that transmits the signals via wired or wireless means to the external device 400.

In an example embodiment and in FIG. 1, the apparatus 100 comprises a motion activated switched 126 facing the eyebrows of the user 110. When the user 110 moves his or her eyebrow, the motion activated switched 126 will detect the movement and convert it to an electric current that further gets amplified, filtered and processed to a digital signal. The digital signal is transmitted to the digital signal processor of the driver 106. The driver 106 transmits the signals to the communication module 300 that transmits the signals via wired or wireless means to the external device 400.

In an example embodiment and in FIG. 1, the apparatus 100 comprises an airflow-activated switch 127 facing the mouth or the nose of the user 110. The airflow-activated switch comprises a tubular housing 128 that houses mobile parts and fixed parts. When the user 110 blows air out of his or her mouth or nose, the air flow moves the mobile parts to close an electric circuit or generate an electric current which in turn activated switched 127 to detect the air flow and convert it to an electric current that further gets amplified, filtered and processed to a digital signal. The digital signal is transmitted to the digital signal processor of the driver 106. The driver 106 transmits the signals to the communication module 300 that transmits the signals via wired or wireless means to the external device 400.

In an example embodiment and in FIG. 1, the apparatus 100 comprises a front facing camera 130 mounted on the body 101 and facing the external world at which the user 110 is looking. The images acquired by the camera 130 are converted to digital data. The digital data is transmitted via wired or wireless means to the external device 400. The software 600 uses the data generated by the optoelectronic sensor 102 to determine the direction of gaze. The software 600 may allow the user 110 to fixate on different objects in the external world and calibrates the direction of gaze of the user 110 as obtained by the optoelectronic sensor 102 to the acquired images of the environment. After such calibration, the software would be able to superimpose the direction of gaze on the successively captured images of the environment by the front facing camera 130 to determine what object or objects the user is looking at.

In an example embodiment and in FIG. 1, the apparatus 100 comprises a back facing camera 135 mounted on the body 101 and facing one or both eyes 112 of the user 110. The back facing camera 135. The camera may further comprise illumination means such as infrared illumination. The images acquired by the camera 130 are converted to digital data. The digital data generated by the camera is transmitted via wired or wireless means to the external device 400. The software 600 may use eye-tracking algorithm of one or both eyes well known from prior art to be used as supplemental means of eye tracking. For example when the user 110 blinks the lid blocks the view of the optical array sensor 102, and the eye 112 may move underneath the closed lid before the eyelid opens causing un-captured eye movement. Once the user 110 opens his or her eyelid, the eye may be in a new position. The software 600 can detect and compensate for the un-captured movement by comparing the position of the eye 112 before and after each blink to recalibrate the eye tracking. The device may also combine the eye tracking data from the camera 135 analyzed by the software 600 and the tracking data obtained by the optoelectronic array sensor 102 and use one or more mathematical combination of both data.

The successive images of the eye 112 captured by the conventional back facing camera 135 are processed by the external device 400 which utilizes a software 600 to generate the absolute co-ordinates of the eye in its socket based on recognizing one or more of the eye features within the captured frame such as the illuminated pupil. The eye tracking data obtained via this method is generated at a much lower rate for example 16-250 frame per second given the low refresh rate of the camera compared to the tracking data obtained via the optical array sensor 102 with frame rates of at least 1500 frame per second. The software can combine the slow absolute co-ordinates of the eye within each frame obtained from the back facing camera with the fast relative eye movement co-ordinates generated by the frame to frame changes obtained from the opto-electrical array sensor 102 to improve the accuracy and the speed of eye tracking.

The eye tracking data obtained from the optoelectrical array sensor 102 and or the back facing camera 135 as well as the successive frames captured by the front facing camera 130 can be processed by the software 600 of the external device 400 to superimpose a visual marker of the position of gaze of the user on the images acquired by the front facing camera to indicate the area the user is looking at.

In an example embodiment and in FIG. 1, the apparatus 100 comprises a gyroscopic module 138 mounted on the body 101. The gyroscopic module may comprise one or more gyroscopic sensor. It may comprise one or more accelerometer s arranged in a way such that acceleration, rotation and movement in the X, Y and access are sensed. As the body 101 of the device in the frame moves in unity with the head of the user 110, the gyroscopic module senses the movement of the user's head in the horizontal, vertical, antero-posterior and rotational directions. The digital data generated by the gyroscopic module 138 is transmitted via wired or wireless means to the external device 400. The software 600 uses the head movement tracking data generated by the gyroscopic module 138 in conjunction with the head tracking data generated by the optoelectronic array sensor 102. When the user 110 fixates on an object and moves his or her head, the vestibulo-ocular reflex moves the eyes in opposite direction so that the optoelectronic array sensor 102 sensed eye tracking data can be processed by the external device software 600 can be used for head movement tracking. The data generated by the gyroscopic sensor as well as the optoelectronic array sensor 102 can be further processed by the external device software 600 in one or more mathematical way to use one or both sets of data to improve the accuracy of head movement tracking.

In an example embodiment and in FIG. 1, the apparatus 100 comprises a feedback module 139 mounted on the body 101. The feedback module 139 may comprise is a sound speaker, buzzer, vibrator and/or a light source. When the user 110 uses a gesture such as a blink of certain character, eyebrow movement, air blowing or the same the feedback module 139 may generate a sound, light, or vibration to inform the patient that his or her gesture has been received. The feedback module 139 may be activated by a short loop feedback from the driver 106 or may be activated by a long loop feedback from the external device 400.

Figure 2:
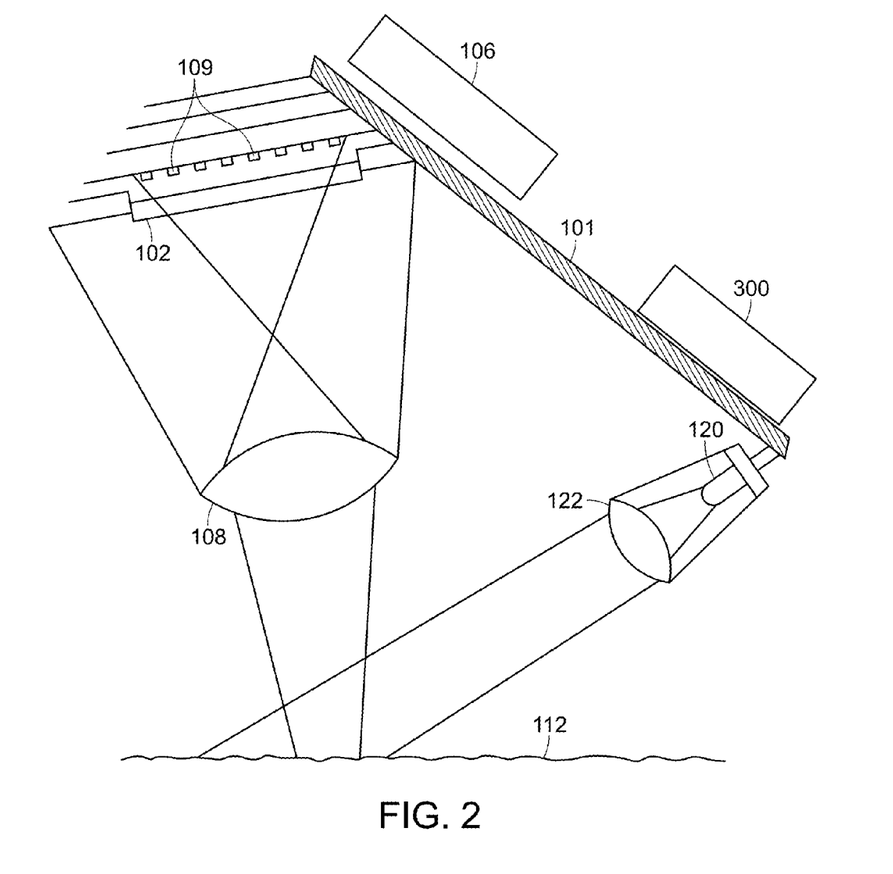
FIG. 2 is a schematic drawing of the optoelectronic array sensor along with the source of light attached the body frame in front of the subject eye.

The sensor 102 of FIG. 2 is made of an array of optoelectronic elements. In an example embodiment, unlike in FIG. 1, the sensor also forms the body 101. The sensor can be attached to the head e.g. by adhesive material such as tape or by forming it suitably to conform to the shapes of the face so that the sheet attaches to the head sufficiently to remain in place at least when the user 110 remains still.

In an example embodiment and in FIG. 1, the sensor is attached to a lens or to the frame of eyeglasses so that the sensor 102 resides between the eye of the user and a lens of the eyeglasses, when the eyeglasses are worn by the user. In an alternate example embodiment, the sensor is integrated with a lens of eyeglasses.

In an example embodiment and in FIG. 2, the sensor 102 is attached to a focusing lens 108 to form an image of the surface of the eye on the sensor.

In an example embodiment and in FIG. 2, the light source 120 is attached to a collimating lens 122 to evenly illuminate the surface of the eye adjacent to the sensor.

In an example embodiment, the photo-electronic sensor array is selected from a group comprising of optoelectronic material such as pairs of complementary metal-oxide semiconductor CMOS to form an array of monochromatic pixels such as 16×16 or 32×32 pixels.

The apparatus 100 comprises, in an example embodiment, a flexible printed circuit (FPC) configured to operatively connect the sensor 102 to the driver 106. The flexible printed circuit can be used to enable hinging of the frame 101 as with normal eyeglasses. In an alternative embodiment, the apparatus 100 comprises a printed wiring board (PWB) configured to operatively connect the sensor 102 to the driver 106. For instance, the driver 106 can reside at a lower, upper portion or the side arms of a frame surrounding the frame lens or in the middle part of the frame 101 bridging the left and right lenses over the nose 114 of the user 110.

The apparatus 100 of FIGS. 1 and 2 comprises an analog-to-digital converter configured to convert analog signals produced by the sensor 102 to digital signals. The analog-to-digital converter is embodied in an example embodiment in the driver 106. Alternatively, in other example embodiments, the analog-to-digital converter resides on the flexible printed circuit may comprise the driver or on the printed wiring board. The driver can also be either separated or combined with the flexible printed circuit or with the printed wiring board.

In an example embodiment and in FIG. 2, the body 101 is configured to support the optoelectronic array sensor 102 in front of the eye 112 of the user 110 at a proximate distance. The proximate distance is, for instance, such that the eyelash of the user does not reach to the sensor in front of the eye. The proximate distance can also be adjustable to allow for proper focusing of the sensor 102. In an example embodiment and in FIG. 2, the proximate distance corresponds to the distance of normal eyeglass lenses from the eyes 112 of the user 110.

In an example embodiment, the apparatus 100 further comprises a touch controller 121 for detecting touching of the user at one or more touch sensitive areas of the apparatus 100. The touch sensitive areas are provided in the body and/or on the driver. Thus, the user can be allowed to provide commands or information by touching one or more parts of the apparatus 100. In other example embodiments, the commands may relate to controls of an application running in the apparatus 100 or at an external device.

In an example embodiment and in FIGS. 1 and 2, the apparatus 100 comprises two of the sensors 102. The apparatus 100 is then configured support one of the sensors in front of each of two eyes of the user. In an alternative two-eye implementation, the apparatus has one extended sensor that extends over both eyes of the user.

For communicating with external devices, the apparatus has a connection interface 300 in some example embodiments. Then, the apparatus can provide the external device with eye tracking signals corresponding to the detected eye movements as well as touch information.

In an example embodiment, the communication interface comprises a wired connection interface. The wired connection interface is, for example, compliant with a standard, such as Inter-Integrated Circuit (I2C) protocol, Serial Peripheral Interface (SPI), Universal serial bus (USB) or IEEE-1394.

In an example embodiment, the apparatus is configured to receive operating power from the external device. The power can be received through the wired communication interface. For instance, USB and IEEE-1394 readily provide for power transfer simultaneously with data transfer.

In an example embodiment, the communication interface comprises a wireless connection interface. The wireless connection interface is, for instance, compliant with a standard such as low power Bluetooth, IEEE 802.11 (wireless LAN), ultra-wide band (UWB) radio link or Infrared Data Association (IrDA) link.

The apparatus 100 or an external device communicatively connectable with the apparatus (wirelessly or with wires) comprises in an example embodiment an external device 400 configured to use eye tracking information produced by the apparatus 100 for controlling an application, function of a controllable entity or a service accordingly.

The external device 400 comprises a communication interface, a processor coupled to the communication interface module, and a memory coupled to the processor. The memory comprises a work memory and a non-volatile memory such as a read-only memory, flash memory, optical or magnetic memory. In the memory, typically at least initially in the non-volatile memory, there is stored software operable to be loaded into and executed by the processor. The software may comprise one or more software modules and can be in the form of a computer program product that is software stored in a memory medium. The external device 400 further comprises a 102 and a driver 106 each coupled to the processor (when exemplifying the apparatus 100, but not necessarily when exemplifying an external device).

It shall be understood that any coupling in this document refers to functional or operational coupling; there may be intervening components or circuitries in between coupled elements.

Figure 3:
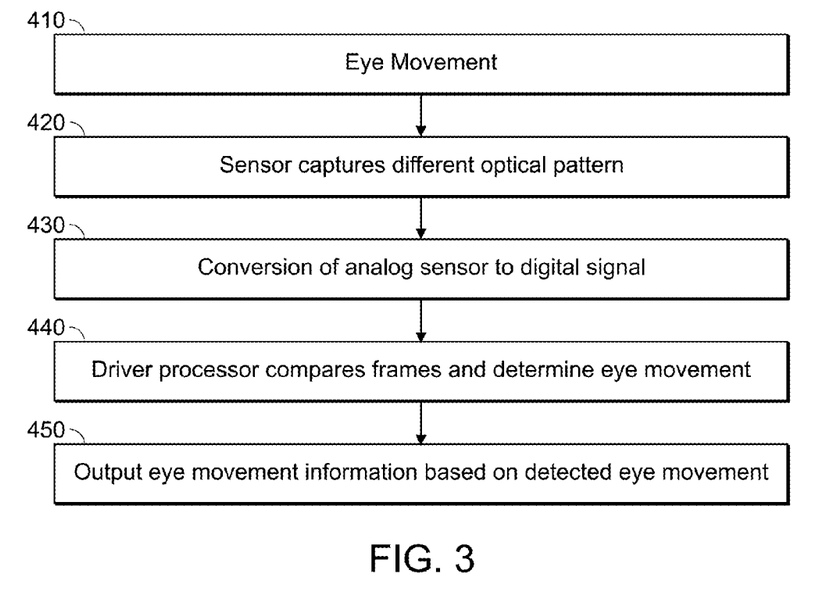
FIG. 3 shows a schematic flow chart illustrating a process according to an example embodiment.

The communication interface module 300 is configured to provide local communications over one or more local links. The links may be wired and/or wireless links. The communication interface 300 may further or alternatively implement telecommunication links suited for establishing links with other users or for data transfer (e.g. using the Internet). Such telecommunication links may be links using any of: wireless local area network links, Bluetooth, ultra-wideband, cellular or satellite communication links. The communication interface 300 may be integrated into the device 400 or into an adapter, card or the like that may be inserted into a suitable slot or port of the device 400. While FIG. 3 shows one communication interface 300, the device may comprise a plurality of communication interfaces 300.

The processor of the device is, for instance, a central processing unit (CPU), a microprocessor, a digital signal processor (DSP), a graphics processing unit, an application specific integrated circuit (ASIC), a field programmable gate array, a microcontroller or a combination of such elements. The device 400 may comprise a plurality of processors.

As mentioned in the foregoing, the memory may comprise volatile and a non-volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. In some example embodiments, only volatile or non-volatile memory is present in the device 400. Moreover, in some example embodiments, the device comprises a plurality of memories. In some example embodiments, various elements are integrated. For instance, the memory can be constructed as a part of the device 400 or inserted into a slot, port, or the like. Further still, the memory may serve the sole purpose of storing data, or it may be constructed as a part of an apparatus serving other purposes, such as processing data. Similar options are thinkable also for various other elements.

Figure 4:
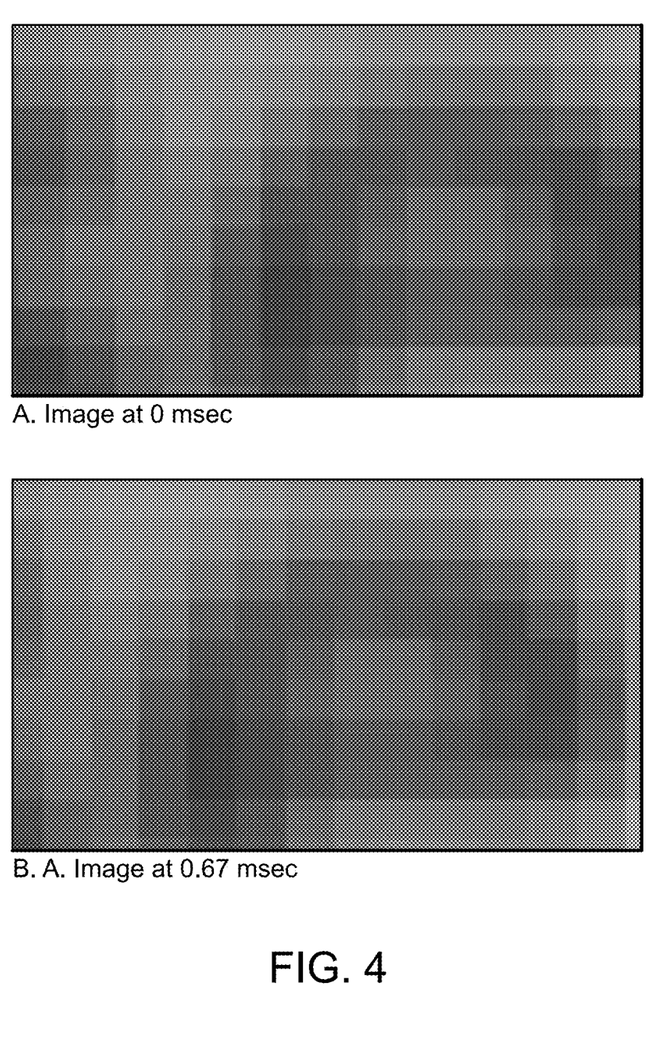
FIG. 4 shows 2 frames acquired by the optoelectronic sensor at 2 successive points of time.

A skilled person appreciates that in addition to the elements shown in FIG. 4, the device 400 may comprise other elements, such as microphones, displays, as well as additional circuitry such as further input/output (I/O) circuitries, memory chips, application-specific integrated circuits (ASIC), processing circuitry for specific purposes such as source coding/decoding circuitry, channel coding/decoding circuitry, ciphering/deciphering circuitry, and the like. Additionally, the device 400 may comprise a disposable or rechargeable battery (not shown) for powering the device when external power if external power supply is not available.

FIG. 3 shows a schematic flow chart illustrating a process according to an example embodiment.

In step 410, the eye 112 moves i.e. turns in its orbit so that the surface of the eye moves with respect to the sensor 102. In response, the sensor 102 detects 420 a change in the position of the eye and produces respective or respectively changed analogue signals to the driver 106. The driver or an intervening analogue-to-digital converter converts 430 the analogue signals into digital form. Armed with the digital signals, the driver 106 determines 440 how the eye 112 has moved and outputs 450 corresponding eye tracking information.

FIG. 4 shows 2 frames obtained by the optoelectronic sensor of the eye surface at 0 msec (A), then at 0.67 msec (B). During this interval of time, the eye of the user has moved within its socket. The movement results in a change in the features and shadows acquired by the sensor 102. The change in the frames will be processed by the driver 106 to estimate the degree and direction of eye movement.

Figure 5:
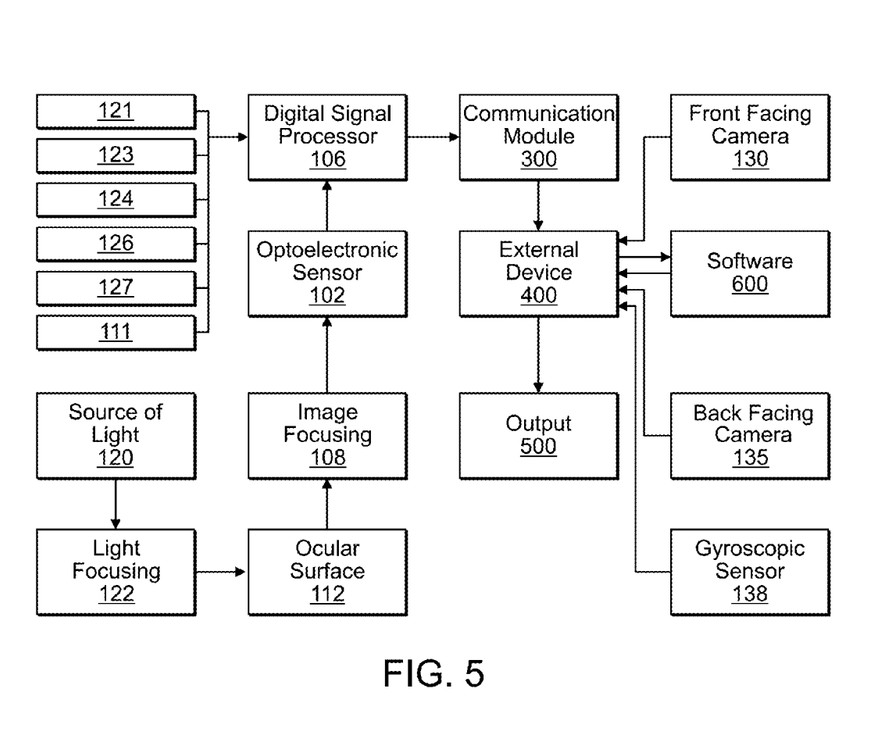
FIG. 5 shows a schematic flow chart illustrating the interaction of the different components of the system according to an example embodiment.

FIG. 5 shows that the source of light 12 shines light that with the aid of the light focusing (collimating) lens illuminates the ocular surface 112 adjacent to the image focusing lens 108 that forms a magnified image of the ocular surface 112 on the optoelectronic array sensor 102. The image formed on the sensor will stimulate the monochromatic pixels of the array sensor depending on the optical texture of the ocular surface adjacent to the sensor. The signals from the sensor transfer to the driver 106, which comprises a digital signal processor, such as an image-processing chip. The frames acquired by the sensor 102 get transferred in rapid succession to be digitized and compare the frames. The image-processing chip mathematically process these frames using cross correlation to calculate how much each successive image is offset from the previous one. The driver 106 will generate digital data of how far the eye has moved and in which direction. The driver will generate the data as shift of the horizontal (X) and vertical (Y) co-ordinate from the last known location. Such data is provided to the communication module 300. The communication module 300 sends wired or wireless data to a port in the device 400 for an example a computer. The computer is equipped with software 600 to process the data acquired. The data is processed and will be directed to an output terminal 500 such as a computer screen. The input devices such as the Blink detector 111, touch controller 121, sound activated switch 123, voice recognition module 124, motion activated switched 126, and air flow activated switch 127 when activated by corresponding gestures from the user 110 will send digital signals to the driver 106. The driver 106 sends the signals after appropriate processing to the communication module 300 then to the external device 400. The software 600 will process these gestures in a way so that the gestures are translated to a particular function such as choice selection, mouse click, flipping to the next page or so. The front facing camera 130, the back facing camera 135 and the gyroscopic module sensors generate digital data that gets communicated to the external device 400 via wired or wireless means to be further processed by the software 600.

Figure 6:
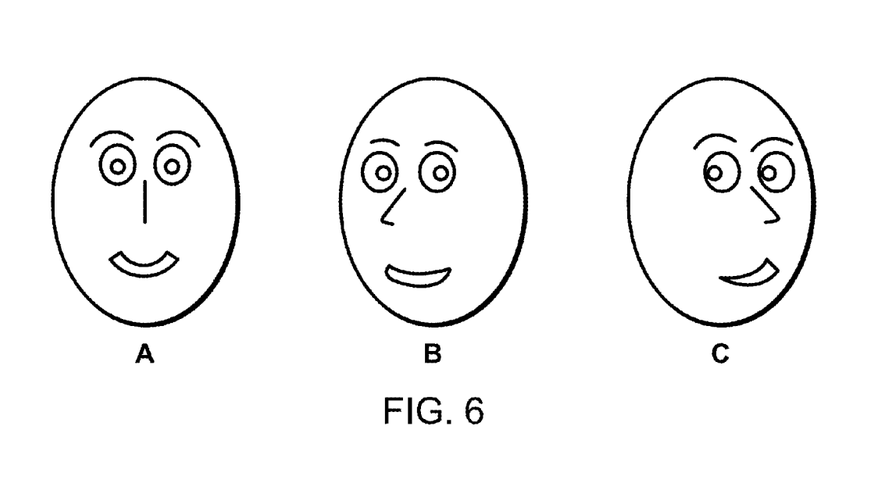
FIG. 6 shows the vestibulo-ocular reflex movement of the eyes to compensate for the change in head position

FIG. 6 shows the vestibule-ocular reflex movement of the eyes to compensate for the change in head position. The FIG. 6 A shows a subject fixating at a target that is straight ahead so the eyes are looking forwards. When the subject turns his or her head to the right (FIG. 6 B), the nervous system sends signals to the muscles controlling the eye position to turn both eyes to the left so that the eyes are still fixating at the same target. When the subject turns his or head to the left (FIG. 6. C), the eyes would turn to the right to compensate for the head movement. The same principal applies when the subject moves his or her head vertically and/or tilts the head. When the head is tilted the eyes turn in the eye sockets along their antero-posterior axis in a movement called cyclotorsion. As the optoelectronic sensor is mounted on the spectacle frame body that moves along with the head, such compensatory eye movements will be sensed by the sensor as eye movements. Cyclotorsion will be sensed as a movement in both the vertical and horizontal axes.

The eye tracking information is used according to different example embodiments a wide variety of disciplines use eye tracking techniques, including cognitive science, psychology (notably psycholinguistics, the visual world paradigm), human-computer interaction (HCI), marketing research and medical research (neurological diagnosis). Specific applications include the tracking eye movement in language reading, music reading, human activity recognition, the perception of advertising, and the playing of sport. Uses include: Cognitive Studies, Medical Research, Laser refractive surgery, Studying Human Factors, Computer Usability, Translation Process Research, Vehicle Simulators, In-vehicle Research, Training Simulators, Fatigue Detection, Adult Research, Infant Research, Adolescent Research, Geriatric Research, Primate Research, Sports Training, Functional Magnetic resonance Imaging (fMRI), Commercial eye tracking (web usability, advertising, marketing, automotive, etc.), Finding good clues, Communication systems for the disabled, Improved image and video communications, Product development, Employee training, Computer Science: Activity Recognition and visual reality.

For example, the ocular movements sensed by the motility tracking device once communicated to an external computer device, can be processed with computer software to analyze the ocular motility for medical or research purposes.

Yet in another example, the ocular movements sensed by the motility tracking device once communicated to an external computer device, can be processed with computer software to move a cursor on the screen so that the tracker serves as a pointing device for the user to control the computer device. It can also be used to select different options on the video display glasses. The touch control and/or the sound activated switch can be activated by the user via touch, sound, voice commands, eyebrow movements, nose or mouth air blowing, and or pressing on a mechanical switch to choose or activate selections on the computer screen.

The device not only can dense voluntary ocular movements, but can also sense involuntary movements such as vestibule-ocular reflex movements. For example, if the user is fixating on a target such as an icon on the computer monitor. The user wants to move a computer cursor to point to the icon on the screen to activate it. The user can stimulate the sensor by either looking towards the cursor in the screen then towards the icon so the sensor will sense the voluntary movement and move the cursor accordingly. The device can also be activated by visually fixating on the target say icon on the computer monitor then moving the head in the direction of the cursor. Such head movement will stimulate the vestibuo-ocular reflex to rotate the eye in an opposite direction to the head movement and to proportionate amplitude. The sensor will sense such ocular movement and will move the cursor without looking away from the object of regard.

Without in any way limiting the scope, interpretation, or application of the claims appearing below, a technical effect of one or more of the example embodiments disclosed herein is that the eyes of a user can be tracked with contactless arrangement. Another technical effect of one or more of the example embodiments disclosed herein is that the contactless arrangement can be portable. Another technical effect of one or more of the example embodiments disclosed herein is that further sensory determinations can be made in conjunction with eye tracking.

Embodiments of the present invention may be implemented in software, hardware, application logic or a combination of software, hardware and application logic. The software, application logic and/or hardware may reside on a driver and/or on an external device communicatively connected with the driver. In an example embodiment, the application logic, software or an instruction set is maintained on any one of various conventional computer-readable media. In the context of this document, a "computer-readable medium" may be any media or means that can contain, store, communicate, propagate or transport the instructions for use by or in connection with an instruction execution system, apparatus, or device, such as a computer, with an example of a computer. A computer-readable medium may comprise a computer-readable storage medium that may be any media or means that can contain or store the instructions for use by or in connection with an instruction execution system, apparatus, or device, such as a computer.

If desired, the different functions discussed herein may be performed in a different order and/or concurrently with each other. Furthermore, if desired, one or more of the above-described functions may be optional or may be combined.

For the purposes of promoting an understanding of the principles of the invention, reference has been made to the preferred embodiments illustrated in the drawings, and specific language has been used to describe these embodiments. However, this specific language intends no limitation of the scope of the invention, and the invention should be construed to encompass all embodiments that would normally occur to one of ordinary skill in the art. The particular implementations shown and described herein are illustrative examples of the invention and are not intended to otherwise limit the scope of the invention in any way. For the sake of brevity, conventional aspects of the system (and components of the individual operating components of the system) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. An apparatus for tracking eye and head movement comprising:
   a. at least one optoelectronic array sensor or optical flow sensor formed of a plurality of optoelectronic sensor cells and comprising an image sensor chip connected to a processor programmed to run an optical flow algorithm or a vision chip including an integrated circuit having both an image sensor and a processor on a same die;
   b. a body configured to support the at least one optoelectronic array sensor with focusing means along with a source of light with collimating means in front of and in proximity to an eye of a user and configured to adjust a distance between the at least one optoelectronic array sensor and the eye of the user to allow for proper focusing of the at least one optoelectronic array sensor;
   c. an optical focusing means to focus an image of the ocular surface of the user on the at least one optoelectronic array sensor in front of the eye of the user at a proximate distance corresponding to a focusing power of the optical focusing means such that an eyelash of the user does not reach to the optical focusing means in front of the eye, wherein a focusing distance to the at least one optoelectronic array sensor is adjustable to maintain a focused image of the ocular surface including an optical texture of the ocular surface formed by irregularities comprising one or more of the group consisting of optical imperfections, conjunctival blood vessels, conjunctival glands and uneven thickness of the tear film, the focused image of the ocular surface forming a corresponding image on the at least one optoelectronic array sensor with distinct shadows;
   d. a focusing lens with a source of light;
   e. a means to detect blinking;

f. a driver configured to receive signals from the sensor array to generate coordinate signals corresponding to changes in the position of the ocular surface relative to the sensor array;

g. a means to detect user's additional input and gestures and one or more of the group comprising a sound activated switch; a motion-activated switch facing the eyebrows and attached to the body of the apparatus; a voice recognition module configured to receive voice commands from the user; an airflow-activated switch attached via mechanical means to the body of the apparatus and facing the mouth of the user; a mechanical switch; a front facing camera attached to the body of the apparatus; a back facing camera attached to the body of the apparatus; a feedback device attached to the body of the apparatus; and combinations thereof; and h. wherein the apparatus is computer controlled and provides an output indicative of an amount and direction of eye movements in an orbit of the eye to move a cursor on a computer screen as a pointing device for the user to control a computer device, enabling the user to use the apparatus to perform one or more of the group consisting of moving a computer cursor to point to an icon on a screen to activate the icon, selecting different options on a video display, and using gestures to control the computer device.

2. The apparatus of claim 1 wherein the amount and direction of eye movements in its orbit are measured.

3. The apparatus of claim 1 wherein the amount and direction of head movements are measured.

4. The apparatus of claim 1 wherein the image of the ocular surface of the user on the at least one optoelectronic array sensor will stimulate monochromatic pixels of the at least one optoelectronic array sensor depending on the optical texture of the ocular surface adjacent to the at least one optoelectronic array sensor.

5. The apparatus of claim 4 further comprising;
a. a driver configured to receive signals from the sensor and to detect shift of the image of the ocular surface formed on the sensor array to determine eye movements based on the received signals;
b. an external device with software comprising code for receiving signals from the driver connected to an optoelectronic array sensor located in front of an eye of a user; and
code for determining movement of the eye based on the received signal; the external device is attachable to a computer device via an interface to communicate the movement parameters to the computer device; and
c. a communication module to communicate with the external device, wherein the external device is provided with eye tracking signals and user's additional input and gestures collected by the apparatus.

6. The apparatus of claim 5 wherein the data generated by the eye tracking algorithm of the images captured by the back facing camera and the data generated by the at least one optoelectronic array sensor can be further processed by the external device software in a mathematical way to use one or both sets of data to improve the accuracy of eye movement tracking and detect and compensate for un-captured movement by comparing position of the eye before and after each blink to recalibrate eye tracking.

7. The apparatus of claim 5 wherein the eye tracking data can be further processed by the external device software in a mathematical way to superimpose a visual marker of the position of gaze of the user on the images acquired by the front facing camera.

8. The apparatus of claim 5 further comprising a wireless or wired connection interface for connecting to the external device.

9. The apparatus of claim 5 wherein the means to detect user's additional input comprises a gyroscopic sensor attached to the body of the apparatus wherein the gyroscopic sensor generates data based on head movement tracking.

10. The apparatus of claim 9 wherein the data generated by the gyroscopic sensor and data generated by the optoelectronic array sensor can be further processed by the external device software in a mathematical way to use one or both sets of data to improve the accuracy of eye movement tracking.

11. The apparatus of claim 1 wherein the optical focusing means is selected from the group comprising a focusing lens, mirror, pinhole or a combination thereof.

12. The apparatus of claim 1 wherein the optical focusing means comprises a plus powered focusing lens and the proximate distance corresponds to a distance of normal eyeglass lenses from the eyes of the user.

13. The apparatus of claim 12 wherein the apparatus is wearable by a user as eyeglasses and wherein the at least one optoelectronic array sensor is integrated with the eyeglasses, attached to the eyeglasses frame or attached to the eyeglasses lens.

14. The apparatus of claim 1 wherein the source of light is selected from the group comprising laser emitting diode; visible laser light; light emitting diode of visible light; light emitting diode of invisible light; light emitting diode of a single color, light emitting diode of multiple colors; at least one incoherent light emitting diode; at least one coherent light emitting diode; or combinations thereof.

15. The apparatus of claim 14 wherein the source of light comprises a combination of more than one coherent light emitting diodes that emit a visible light and incoherent light emitting diodes, wherein incoherent light of the source of light projects light on the ocular surface so that different irregularities of the ocular surface along with shadows are more evident and coherent light of the source of light projected on the ocular surface is reflected back to the at least one optoelectronic array sensor forming different laser patterns based on ocular surface irregularities.

16. The apparatus of claim 14 wherein the source of light comprises a combination of more than one light emitting diodes that emit a visible light and light emitting diodes that emit an invisible light.

17. The apparatus of claim 1 wherein the means to detect blinking is comprised of an infrared diode emitting the infrared light at a certain frequency of pulses per second and a photodiode sensitive to the light emitted by the source of lights wherein the infrared diode and photodiode are arranged in a way so that the light emitted by the diode is directed towards the eye surface just below the upper eyelid and the photodiode is also pointed towards the eye surface just below the upper eyelid.

18. The apparatus of claim 1 wherein the means to detect blinking is comprised of a source of sonic or ultrasonic waves and a microphone to detect the reflected waves to detect a blink.

19. A method for determining the amount and direction of eye movement comprising:
a. Forming an image of an ocular surface including an optical texture of the ocular surface formed by irregularities comprising one or more of the group consisting of optical imperfections, conjunctival blood vessels, conjunctival glands and uneven thickness of the tear film, illuminated with a source of light from an apparatus, the focused image of the ocular surface forming a corresponding image on the at least one optoelectronic array sensor, to detect eye movements within its orbit with the at least one optoelectronic array sensor or optical flow sensor apparatus;
b. capturing images of the ocular surface including an optical texture of the ocular surface by the at least one optoelectronic array sensor in continuous succession at a high rate of at least 1500 frames per second;
c. converting the frames from analog to digital data;
d. transferring data to a driver comprising an image-processing chip to compare the successive frames to each other;
e. mathematically processing the images using cross correlation to calculate how much each successive image is offset from the previous one and using software to detect and compensate for un-captured movement by comparing position of an eye of the user before and after each blink to recalibrate the eye tracking, and combining the eye tracking data from a camera analyzed by the software and the tracking data obtained by the at least one optoelectronic array sensor and use one or more mathematical combinations of both data to improve accuracy of eye movement tracking;
f. generating digital data of how far the eye has moved and in which direction; and
g. generating the data as shift of the horizontal (X) and vertical (Y) co-ordinate from the last known location.

20. A method for determining the amount and direction of head movement comprising:
a. Forming an image of an ocular surface including an optical texture of the ocular surface formed by irregularities comprising one or more of the group consisting of optical imperfections, conjunctival blood vessels, conjunctival glands and uneven thickness of the tear film, illuminated with a source of light from at least one optoelectric array sensor or optical flow sensor apparatus, the focused image of the ocular surface forming a corresponding image on the at least one optoelectronic array sensor, to detect eye movements within its orbit while the user is fixating at a target;
b. capturing images of the ocular surface including an optical texture of the ocular surface while the user is fixating on a visual target by at least one optoelectronic array sensor or optical flow sensor in continuous succession at a high rate of at least 1500 frames per second;
c. converting the frames from analog to digital data;
d. transferring data to a driver comprising an image-processing chip to compare the frames to each other;
e. mathematically processing the images using cross correlation to calculate how much each successive image is offset from the previous one and using software to detect and compensate for un-captured movement by comparing position of an eye of the user before and after each blink to recalibrate the eye tracking, and combing the eye tracking data from a camera analyzed by the software and the tracking data obtained by the at least one optoelectronic array sensor and use one or more mathematical combinations of both data to improve accuracy of eye movement tracking;
f. generating digital data of how far the eye has moved to compensate for head movement and in which direction; and
g. generating the data as shift of the horizontal (X) and vertical (Y) co-ordinate from the last known location in the same amplitude and reverse direction to the compensatory eye movement.

* * * * *

UNITED STATES PATENT AND TRADEMARK OFFICE
CERTIFICATE OF CORRECTION

PATENT NO. : 10,353,460 B2
APPLICATION NO. : 15/114904
DATED : July 16, 2019
INVENTOR(S) : Tarek A. Shazly et al.

It is certified that error appears in the above-identified patent and that said Letters Patent is hereby corrected as shown below:

In the Claims

Column 20, Claim 20, Line 22, the word "combing" should read ---combining---

Signed and Sealed this
Tenth Day of September, 2019

Andrei Iancu
*Director of the United States Patent and Trademark Office*